US012575872B2

(12) United States Patent
Heym

(10) Patent No.: US 12,575,872 B2
(45) Date of Patent: Mar. 17, 2026

(54) PLASMA PROBE AND METHOD FOR ASSEMBLY OF ITS ELECTRODE

(71) Applicant: Erbe Elektromedizin GmbH, Tuebingen (DE)

(72) Inventor: Johannes Heym, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 715 days.

(21) Appl. No.: 17/861,895

(22) Filed: Jul. 11, 2022

(65) Prior Publication Data

US 2023/0010005 A1     Jan. 12, 2023

(30) Foreign Application Priority Data

Jul. 12, 2021     (EP) .................................... 21184980

(51) Int. Cl.
*A61B 18/04*          (2006.01)
*A61B 18/00*          (2006.01)
*A61B 18/14*          (2006.01)

(52) U.S. Cl.
CPC .. *A61B 18/042* (2013.01); *A61B 2018/00107* (2013.01); *A61B 2018/1405* (2013.01)

(58) Field of Classification Search
CPC ........ A61B 18/042; A61B 2018/00107; A61B 2018/1405
See application file for complete search history.

(56) References Cited

U.S. PATENT DOCUMENTS 3,911,928 A     10/1975  Lagergren
4,156,429 A  *  5/1979   Amundson .......... A61N 1/0565
                                                        607/121

(Continued)

FOREIGN PATENT DOCUMENTS

CN          1870945  A     11/2006
CN          208447766 U      2/2019
                    (Continued)

OTHER PUBLICATIONS

National Intellectual Property Administration, P.R. China; Search Report in corresponding Chinese Patent Application No. 202210816122.2, dated Sep. 18, 2024; 6 pages.
National Intellectual Property Administration, P.R. China; Office Action in corresponding Chinese Patent Application No. 202210816122.2, dated Sep. 25, 2024, 12 pages.

(Continued)

*Primary Examiner* — Linda C Dvorak
*Assistant Examiner* — Abigail Bock
(74) *Attorney, Agent, or Firm* — Fitch, Even, Tabin & Flannery LLP

(57)          ABSTRACT

A plasma probe comprises a hose with a conductor arranged therein that supports an electrode at least at its distal end. The electrode is either directly secured on the conductor or the conductor is provided with a plastic sheathing at least at its distal end by means of which the electrode is held. The electrode can be inserted between the conductor and the plastic sheathing and can be clamped in this manner. After first use the plastic sheathing can be fused to the electrode. The conductor is placed with clearance inside a channel or hollow space of electrode, however, whereby also in case of spot-like contact between the conductor and the electrode due to the gap provided between them apart therefrom the heat transmission from the electrode on the conductor is impeded and thereby the heat introduction in the plasma probe is limited.

16 Claims, 4 Drawing Sheets

(56)     References Cited

U.S. PATENT DOCUMENTS

| | | | |
|---|---|---|---|
| 6,579,289 | B2 | 6/2003 | Schnitzler |
| 7,717,911 | B2 | 5/2010 | Schnitzler |
| 11,185,365 | B2 | 11/2021 | Brockmann et al. |
| 2007/0034211 | A1* | 2/2007 | Hug .................... A61B 18/042 |
| | | | 128/876 |
| 2009/0024122 | A1* | 1/2009 | Fischer ................ A61B 18/042 |
| | | | 600/104 |
| 2010/0114092 | A1 | 5/2010 | Eisele et al. |
| 2012/0172874 | A1 | 7/2012 | Fischer et al. |
| 2013/0261536 | A1 | 10/2013 | Sartor |
| 2017/0303989 | A1 | 10/2017 | Kirwan, Jr. |
| 2019/0167335 | A1 | 6/2019 | Staebler et al. |

FOREIGN PATENT DOCUMENTS

| | | | |
|---|---|---|---|
| DE | 10030111 | B4 | 7/2008 |
| DE | 102017127976 | A1 | 6/2018 |
| EP | 1568325 | A1 | 8/2005 |
| EP | 3769707 | A1 | 1/2021 |
| GB | 2559010 | B | 5/2019 |
| GB | 2580645 | A | 7/2020 |
| JP | 2002301088 | A * | 10/2002 |
| RU | 155589 | U1 | 10/2015 |
| WO | 2005/046495 | A1 | 5/2005 |
| WO | 2017/076721 | A1 | 5/2017 |

OTHER PUBLICATIONS

Extended European Search Report dated Jan. 5, 2022, in corresponding European Application No. 21184980.7, with machine English translation.

Russian State Academy of Intellectual Property, Russian Office Action in corresponding Russian Patent Application No. 2022 118 469, dated May 7, 2025; 11 pages.

Japan Patent Office; Notice of Reasons for Refusal in corresponding Japanese Patent Application No. 2022-111194, dated Jun. 30, 2025; 16 pages.

Federal Service for Intellectual Property (Rospatent); Decision to Grant in corresponding Russian Patent Application No. 2022118469/ 07(038960); dated Oct. 24, 2025; 14 pages.

* cited by examiner

PLASMA PROBE AND METHOD FOR ASSEMBLY OF ITS ELECTRODE

RELATED APPLICATION(S)

This application claims the benefit of European Patent Application No. 21184980.7, filed Jul. 12, 2021, the contents of which are incorporated herein by reference as if fully rewritten herein.

TECHNICAL FIELD

Subject matter of the invention is a plasma probe, particularly an argon plasma probe, as well as a method for assembly of an electrode of this plasma probe.

BACKGROUND

Electrosurgical instruments with electrodes that directly influence on a tissue, are known. For example, WO 2017/076721 A1 discloses a radiofrequency tool having an electrode realized as resection loop. The electrode bent in U-shape is inserted with its two ends in respective holders to which a supply wire is guided respectively. The electrode is crimped or welded to this supply wire, however, in any case mechanically rigidly connected. A conductor insulation of the electrical supply line thereby extends beyond the end of the electrode and insulates the latter relative to an outer jacket.

An instrument for oviduct coagulation is known from EP 1 568 325 A1 that comprises at its distal end an attachment provided with multiple electrodes. These electrodes are connected to a coaxial supply line by means of a coaxial plug. The arrangement consisting of supply line and plug can be freely axially moved in a working channel of an endoscope.

Furthermore, plasma probes exist that consist substantially from a hose connectable to a gas source, the distal end of which is open and serves for emission of a plasma jet. An electrode is arranged in the distal end of the hose that is typically held by means of an electrode holder, e.g. a metal platelet that extends diametrically through the lumen of the hose. The electrode extends in the form of a conductor wire in proximal direction through the lumen of the hose and can be connected to an electrical source in order to create an electrical discharge at the distal end. Plasma probes constructed according to this principle are in addition known from DE 10 2017 127 976 A1, DE 100 30 111 B4 or EP 3 769 707 A1.

A plasma stream originates from the electrode of the plasma probe that shall hit on the tissue to be treated. Because the electrode is arranged in the distal end of the hose, at least a portion of the created thermal energy also reaches the surrounding wall of the distal end of the hose. For protection thereof a ceramic sleeve can be arranged here, as it is, for example, known from WO 2005/046495 A1 mentioned above. The centric support of the electrodes is, however, provided by the metal platelet that transfers heat to the hose and can result in its destruction during longer durations of operation. This is particularly the case, because the electrode has to be rigidly connected with the metal platelet such that a remarkable heat transfer from the electrode to the platelet is provided. This problem arises more than ever, if the metal platelet itself serves as electrode, as for example proposed in DE 100 30 111 B4.

Starting therefrom it is one object of the invention to provide a concept with which a long-term stable plasma probe can be provided in a simple manner. Thereby particular attention shall be turned to the assembly of the electrode.

SUMMARY

This object is solved by means of a plasma probe as well as a method as described herein.

The plasma probe according to one aspect of the invention comprises a flexible hose, that consists of a plastic material, for example, that can comprise a lumen or multiple lumina that extend respectively from the proximal end of the hose up to its distal end. The lumen serves to channel an appropriate gas, preferably an inert gas, e.g. argon, from the proximal end to the distal end. The lumen of the hose is open at the distal end such that the gas can flow out here.

An electrical conductor is arranged inside the hose that extends preferably over the entire length of the hose from the proximal end up to the distal end thereof and is connected to an electrode there. The electrical conductor is provided with a plastic sheathing at least at its distal end. The plastic sheathing can consist of the same plastic as the hose. It is, however, also possible to provide different plastics.

Preferably the electrode is a needle- or rod-like electrode configured straightly that comprises a proximal and a distal end. The electrode is entirely or at least over a portion of its length configured in a hollow manner, i.e. it comprises an interior channel that is open at both ends or closed at the distal end forming a hollow space. The conductor extends with its distal end with play into this hollow space. The electrode is thereby supported by the conductor and in some embodiments of the invention also from the plastic sheathing of the conductor. It is possible to arrange the electrode such that its proximal end extends into the plastic sheathing of the conductor and is fixated axially by the plastic sheathing. In non-used condition the fixation between the plastic sheathing and the electrode can be realized by means of a friction fit. After the first use the plastic sheathing can be fused to the electrode and thereby adhesively connected with it such that a substance bond connection is provided between the proximal end of the electrode and the plastic sheathing.

Preferably the conductor extends with clearance fit into the electrode. Because of the always present slight corrugation or bending of the conductor or also only due to the incomplete alignment between the conductor and the electrode, an electrical contact between the conductor and the electrode is always provided. In addition, the RF-voltage applied to the conductor is so high that a potential gap between the conductor and the electrode can be readily overcome by the current. After the first use a slight material flow between the conductor and the electrode can result at the contact sites such that a substance bond connection similar to a soldered joint or welded joint is formed.

Independent from whether the electrode extends into the plastic sheathing or not, the electrode can be deformed slightly radially inward for fixation on the conductor, e.g. by means of crushing or crimping. Such a deformation can be formed on the distal end of the electrode, on the proximal end of the electrode or in-between. Then the conductor extends in distal direction at least beyond the deformed area.

A plasma probe constructed according to this concept can be simply produced. The production comprises the following steps: —Providing a hose that comprises a proximal end and a distal end between which at least one lumen is formed, wherein an electrical conductor is arranged in a hose that extends from the proximal end of the hose up to its distal end that comprises a plastic sheathing, —optionally removing the plastic sheathing from a distal section of the hose such that it is exposed, —providing an electrode that comprises at least an end configured in a hollow manner, —pushing the hollow end of the electrode on the end of the conductor that is preferably released from the plastic sheathing, inserting the hollow end of the electrode into the plastic sheathing of the conductor. Thus, the electrode can be inserted in the plasma probe and fixated therein in one single assembly step, in that it is only plugged onto the preferably exposed end of the conductor and if necessary inserted in the interstice opening between the conductor and the plastic sheathing. Due to the expansion of the plastic material created thereby, it is under pretension in strong abutment with the electrode.

Preferably the electrode consists of a metal. It can be provided with a coating, particularly on its outer side, particularly a coating from a metal or a metal alloy. Preferably the metal of the coating has a melting temperature that is less than the melting temperature of the material of which the electrode consists. Silver or silver alloys are suitable as coating metal. However, also other metals, particularly metals with low oxidation tendency and/or high electrical and/or thermal conductivity, can be used.

A particular advantage of the structure according to one aspect of the invention is provided by the thermal decoupling of electrode and hose. Also if the electrode gets hot after longer use, it cannot melt the outer hose as a result of thermal conduction. The plasma probe according to one aspect of the invention thus comprises a colder distal end compared with conventional probes allowing a longer lifetime. Also the influence of tissue by means of heat originating from the probe is reduced. In addition, at the two-dimensional connection site between the proximal end of the electrode and the plastic sheathing of the conductor a slight melting of the plastic sheathing and thus a rigid substance bond connection between the electrode and the conductor or its plastic sheathing is established during use.

In addition, the concept according to one aspect of the invention allows an exact axial as well as radial orientation of the electrode. Even though the hose is deformed at its outside during a short term, the positioning of the electrode is not affected thereby.

The lumen surrounded by the hose can be separated into two or more sub-lumina that extend parallel to one another. The separation can extend over the entire length of the hose or only over a length portion. The separation of the lumen in sub-lumina can be realized by walls extending radially or obliquely relative to the radial direction that connect the hose with the plastic sheathing. The walls can contribute to support and hold the conductor inside the hose centrally. Thus, the hose can be manufactured together with the plastic sheathing of the conductor and the at least one connection wall between the hose and the plastic sheathing in one single process, e.g. by plastic extrusion. Preferably thereby only one plastic material is used. It is, however, also possible to use different plastics for the hose and the plastic sheathing and to produce the probe by co-extrusion. In addition, it is also possible to provide the plastic sheathing and the hose as separate elements from identical or different plastic materials. The conductor with its plastic sheathing can be movably arranged inside the hose, e.g. in axial direction and/or in radial direction.

In all of these embodiments no metallic connection exists between the conductor and the electrode on one hand and the hose on the other hand. If a substance joint exists between the plastic sheathing and the hose, this connection is preferably free of metal elements or other good thermal conductive elements. In this manner the thermal conductivity between the electrode and the hose is minimized. In addition, the distal end of the hose can be provided with a preferably electrically insulating temperature-resistant sleeve, e.g. consisting of ceramic, in order to avoid direct contact between the created plasma stream and the hose consisting of plastic.

The electrode only held at its proximal end extends preferably in a cantilever manner away from the conductor in distal direction without projecting out of the lumen of the hose. In doing so, a direct contact between the electrode and biological tissue can be avoided. It is, however, also possible to arrange the electrode in a manner projecting out of the hose, whereby in this case preferably an insulator body is placed on the distal end of the electrode.

BRIEF DESCRIPTION OF THE DRAWINGS

Further characteristics and features of the plasma probe according to aspects of the invention can be taken from the drawing or the following description. The drawings show.

DETAILED DESCRIPTION

Figure 1:
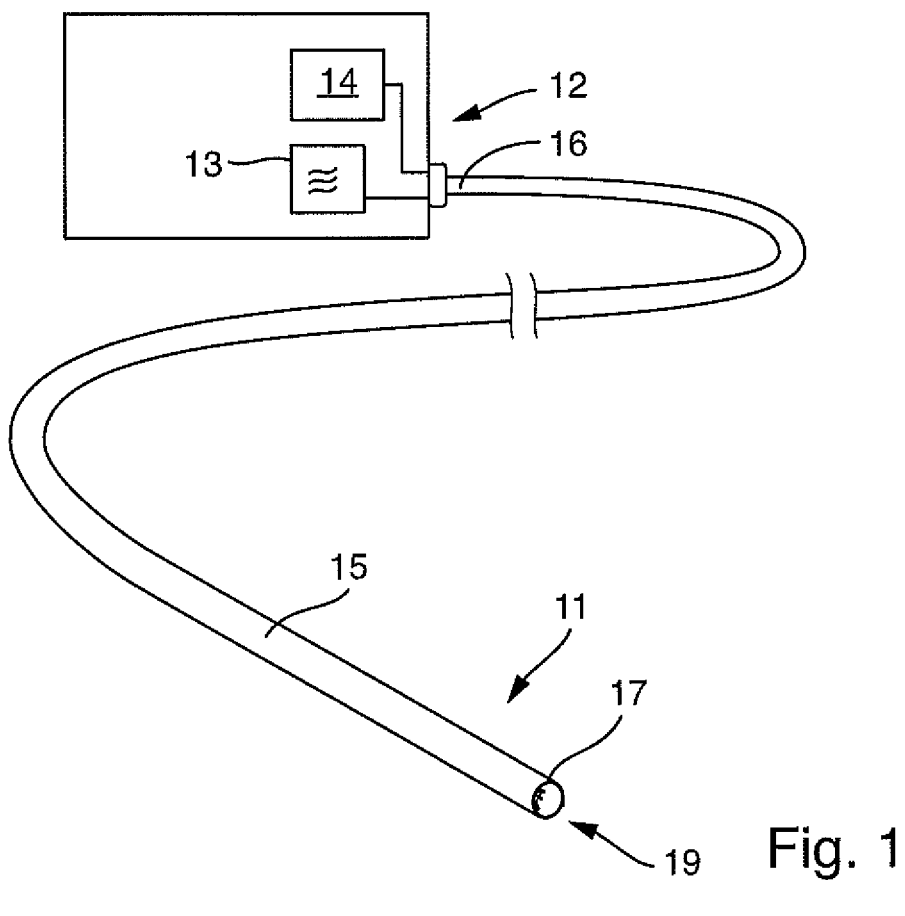
FIG. 1 a plasma probe according to the invention connected to a supplying apparatus in a schematic illustration, FIG. 2 the distal end of the plasma probe in a schematic perspective illustration, FIG. 3 a face side view of the plasma probe according to FIG. 2, FIG. 4 the plasma probe according to FIG. 3 cut along the chain dotted line IV-IV shown in FIG. 3, FIG. 5 a modified embodiment of the plasma probe according to the invention in a longitudinally cut illustration, FIGS. 6-8 further modified embodiments of the plasma probe according to the invention in a longitudinally cut illustration respectively, FIG. 9 a plasma probe having an insulator body in a partly cut side view, FIG. 10 a front side view of a modified embodiment of the plasma probe according to the invention and FIG. 11 a front side view of the further modified embodiment of the plasma probe according to the invention.
Figure 2:
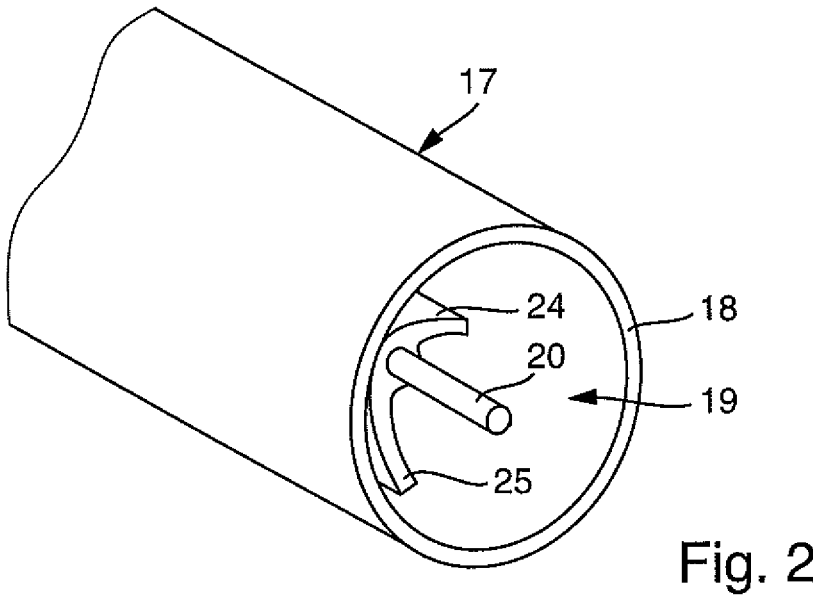

A plasma probe 11 is illustrated in FIG. 1 that is connected to a supplying apparatus 12. The apparatus 12 provides the required operation media and electrical power for the operation of plasma probe 11. For this apparatus 12 comprises a radio frequency generator 13 as well as a gas source 14. This comprises, for example, a pressure regulator and valves via which a gas flow taken from a gas bottle, e.g. an argon flow, can be channeled to the plasma probe 11 in a controlled manner.

The plasma probe 11 comprises a hose 15 that extends from a proximal end 16 up to a distal end 17. The face 18 of the distal end 17 of hose 15 surrounds a plasma exhaust port 19 that emits a plasma jet during operation. By the terms end, distal end and proximal end, end sections are always referred to.

In addition an electrode 20 is arranged in the plasma exhaust port 19 that is electrically connected with the RF generator 13. For this purpose serves an electrical conductor 21, e.g. apparent from FIGS. 3 and 4, that extends along the entire length of hose 15 from its proximal end 16 to its distal end 17. The electrode 20 can consist in all embodiments of a temperature-resistant material, e.g. stainless steel. In addition, it can be provided with a coating in all embodiments, particularly a coating the melting temperature of which is preferably less than the melting temperature of electrode 20. Particularly the coating can consist of silver or a silver alloy.

The conductor 21 can be realized by a monofilament wire, e.g. a stainless steel wire, or also by a wire made of another material. The conductor 21 is thereby provided with a plastic sheathing 22, at least along a part of its length that preferably surrounds the conductor 21 over its entire circumference (360°). The plastic sheathing 22 can thereby extend over the entire length of the conductor up to its distal end 23. The distal end 23 of conductor 21 itself can be exposed, i.e. released from the plastic sheathing. The exposed section can have a length of one or multiple millimeters. Starting from the distal end 23 the plastic sheathing 22 extends at least a few centimeters in proximal direction. However, it can also cover the entire length of conductor 21.

Figure 3:
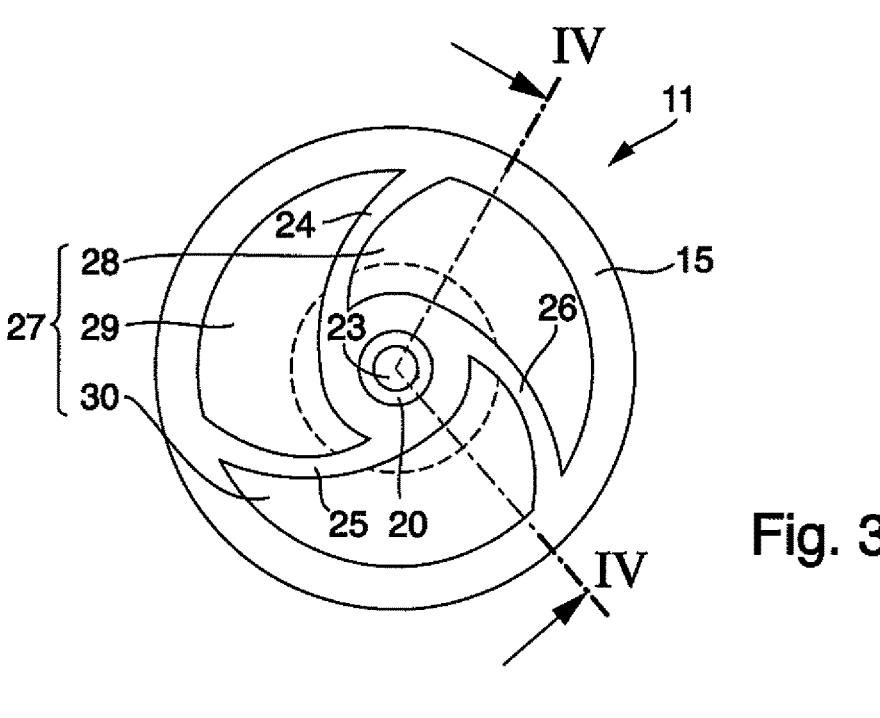
Figure 4:
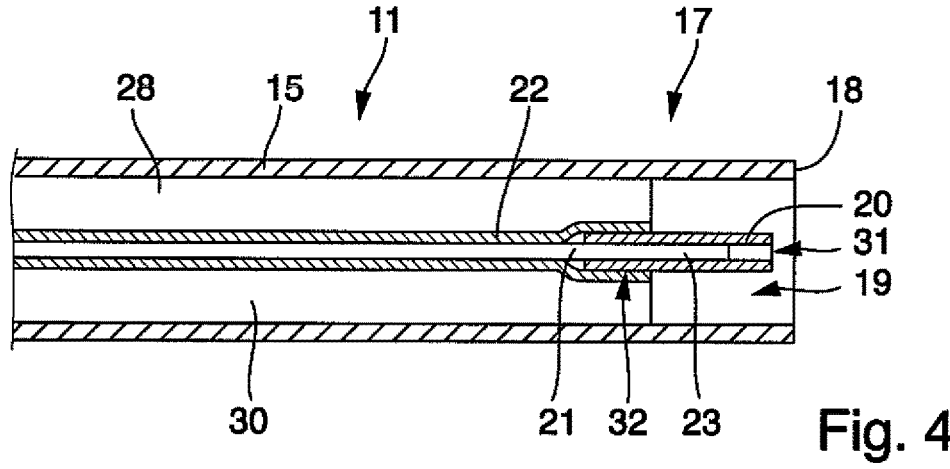

In an embodiment illustrated in FIG. 4 the plastic sheathing 22 is connected with the hose 15 by means of at least one, preferably multiple walls 24, 25, 26, as apparent from FIG. 3. They separate a lumen 27 enclosed by hose 15 in two or more, in the present case three, sub-lumina 28, 29, 30. The walls 24, 25, 26 can extend inclined relative to the radial direction, as apparent from FIG. 3, or it can also be arranged otherwise. In addition, the walls can be configured in a planar as well as in a curved manner, as illustrated.

The electrode 20 can be realized by means of a metal tube, as illustrated in FIG. 4. It comprises a central channel or hollow space into which the distal end 23 of conductor 21 extends. Preferably thereby the inner diameter of this channel or hollow space is slightly larger than the outer diameter of conductor 21 such that a clearance fit results between them. In the embodiment according to FIG. 4 the electrode 20 is configured in a hollow cylindrical manner and open at its distal end 31. The proximal end 32 of electrode 20 is pushed on the conductor 21 so far that it is inserted between the plastic sheathing 22 and the conductor 21. Thereby FIG. 4 illustrates that the plastic sheathing 22 is released and extended locally from conductor 21, whereby it secures electrode 20 first at least by means of friction fit in doing so. The distal end 23 of conductor 21 is loosely arranged inside the channel or hollow space of electrode 20 and thereby first abuts selectively against electrode 20. Preferably the connection between conductor 21 and electrode 20 is loose in axial direction, i.e. not tensile force transmitted.

In all embodiments described above or in the following having a sleeve-shaped electrode 20 it can have a face that is orientated obliquely to its longitudinal direction. The tube-shaped electrode 20 can be cut at its distal end obliquely to its axis for this purpose comparable to the distal end of the cannula of a syringe.

Independent from the inclination of the face of electrode 20, the supply line can extend through the electrode 20 and can project beyond the distal end of electrode 20. This can contribute to an improvement of the ignition capability.

The plasma probe 11 described so far can be manufactured, in that first the hose 15 having a conductor 21 arranged therein is provided. For example, the hose 15 having the conductor 21 can be produced like a cable by means of plastic extrusion. From the material provided in this manner the desired length for the plasma probe 11 is cut and the conductor 21 is first exposed at its distal end 23. Thereby the respective material of the plastic sheathing 22 and the walls 24-26 is removed. In doing so, the distal end 23 of conductor 21 is exposed.

In the subsequent process the electrode 20 is now pushed on the exposed distal end 23 of conductor 21 and into the plastic sheathing 22. As can be taken from FIG. 4, electrode 20 thereby urges the plastic sheathing 22 radially outward and is thereby clamped itself. The electrode 20 is now held in a friction-fit manner. The distal end 23 of conductor 21 abuts selectively loosely against the inner wall of electrode 20. Preferably electrode 20 is thereby inserted so far that it is, with view from outside, located behind the distal face 18 of hose 15, i.e. offset proximally relative to this face 18. Now plasma probe 11 is ready for use.

For operation of plasma probe 11 it is connected to apparatus 12. In doing so, the proximal end of conductor 21 is electrically connected with the RF generator 13. The proximal end of lumen 27 is connected with gas source 14. For operation the lumen 27 is supplied with gas, e.g. argon or another inert gas, such that a gas flow is created inside lumen 27 flowing in distal direction. The RF generator 13 supplies electrodes 20 with RF voltage of typically multiple 100 Volts relative to a neutral potential that is applied to the patient to be treated by means of a not illustrated neutral electrode.

Now a so-called spark is created at the electrode 20 with which the discharged gas is ionized such that a plasma jet is formed. The current thereby flows from the conductor 21 via the contact spots between the distal end 23 and the electrode 20 into the electrode 20 and therefrom via the ionized gas to the patient. Thereby the current flow can effect a selective soldering or welding of conductor 21 with electrode 20 and thus a mechanical connection. In addition, the electrode 20 heats remarkably, whereby the plastic sheathing 22 can melt or fuse in the area covering electrode 20. Thereby a substance bond connection is created between sheathing 22 and electrode 20 and/or between the conductor 21 and the electrode 20.

Figure 5:
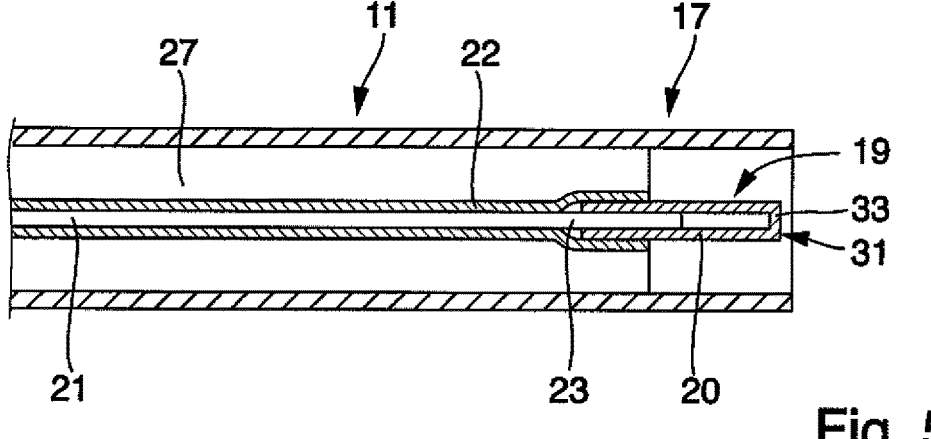

Modifications can be made to plasma probe 11 without leaving the scope of the invention. For example, according to FIG. 5, each of the walls 24, 25, 26 can be omitted. The conductor 21 is located with its sheathing 22 loosely inside lumen 27 and can be axially and/or radially moved therein.

Independent therefrom it is possible to provide electrode 20 with a closed end 33 that forms the distal terminal of electrode 20. Particularly with regard to the connection between conductor 21 and electrode 20, the explanations made above apply accordingly.

Figure 6:
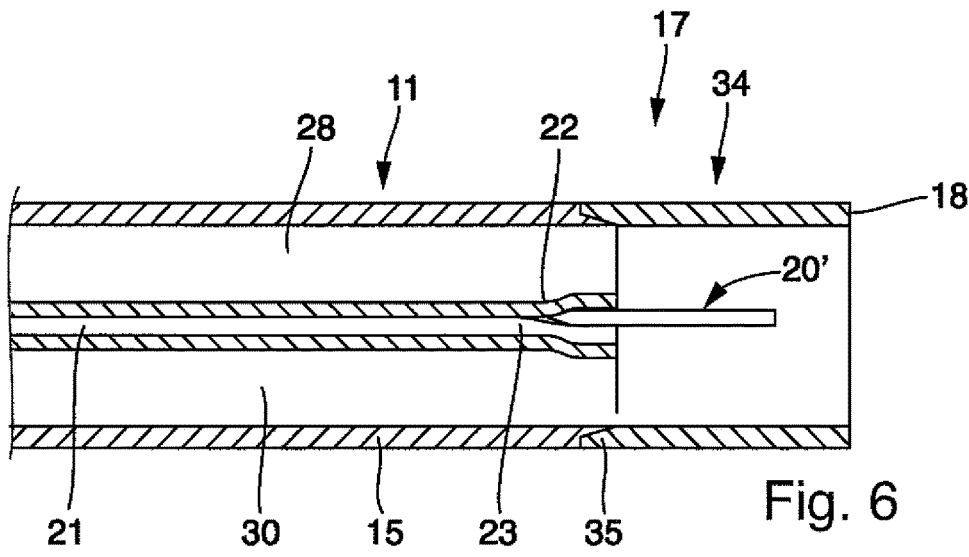

Also with regard to the connection between electrode 20 and conductor 21, numerous modifications are possible. For example, instead of a sleeve-shaped electrode 20 according to FIG. 4 or 5, also a needle- or rod-shaped electrode 20' can be used, as illustrated in FIG. 6. Also this electrode can be inserted between conductor 21 and plastic sheathing 22 and can be clamped thereby. The conductor 21 can be a solid wire, as in the embodiments explained above. However, in this embodiment and also in the embodiments according to FIGS. 3 and 4 described above, a braided wire can be used instead of a solid wire.

In the plasma probe according to FIG. 6, an exposure of the distal end 23 of conductor 21, i.e. the removal of the plastic sheathing 22 in this area, can be omitted. While conductor 21 or its distal end 23 guides the electrode 20 during insertion into the plastic sheathing 22 in the embodiments according to FIGS. 1-4, such a guidance is not necessary in the embodiment according to FIG. 6. The electrode 20' that is preferably pointed at its proximal end is simply punctured in the plastic sheathing 22 in the vicinity of conductor 21.

In all probes according to FIGS. 3-6 the distal end 17 of hose 15 can also be formed by a temperature-resistant sleeve 34, e.g. consisting of ceramic. This is illustrated by way of example in FIG. 6 for all other embodiments. The sleeve 34 can be connected with hose 15 via a tapering seat 35.

Figure 7:
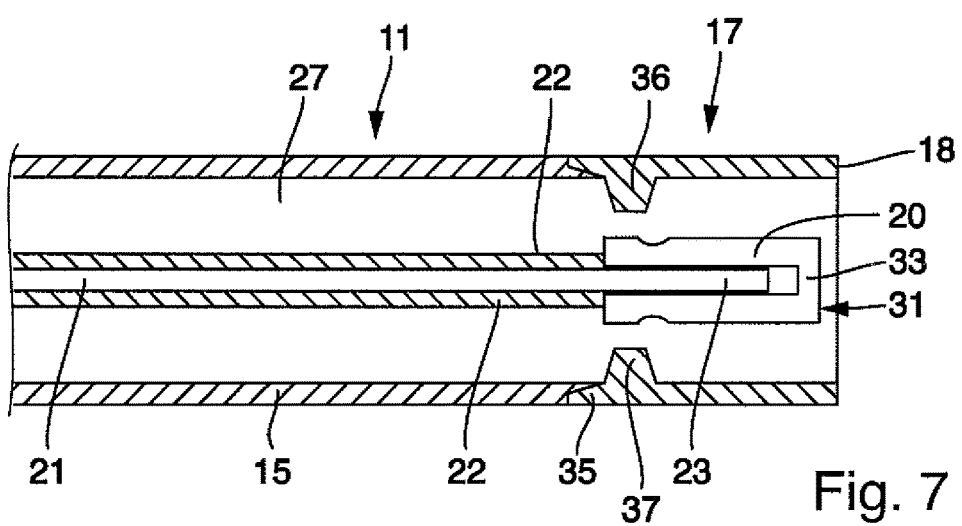

It is not necessarily required to move electrode 20 between conductor 21 and its plastic sheathing 22 and to fixate it by means of clamping. FIG. 7 illustrates an embodiment of plasma probe 11 for this purpose in which electrode 20 is only connected with the distal end 23 of conductor 21 released from the plastic sheathing 22. The electrode 20 can be held in a loss-proof manner on the distal end 23 of conductor 21 due to radial deformation, e.g. crimping or the like. In FIG. 7 only by way of example plasma probe 11 is explained in which the conductor 21 as well as its plastic sheathing 22 and the electrode 20 are not rigidly connected with hose 15. The construction principle having an electrode 20 that is only secured on the conductor 21 can also be realized in any other plasma probe 11 described above. In addition, all of the arrangements of electrode 20, conductor 21 and plastic sheathing 22 described above or in the following can also be used in probes in which no connection between the hose 15 and the plastic sheathing 22 exists. For example, the conductor 21 with its plastic sheathing 22 can be placed inside hose 15 as single-wire cable.

In any probe in which conductor 21 and its sheathing 22 are not connected with the hose 15 the sleeve 34 arranged on the distal end 17 can have three or more noses 36, 37 facing inwardly or another structure that limits the radial movability of electrode 20 or conductor 21. The noses 36, 37 are therefore suitable to effect a sufficient centering of electrode 20. If electrode 20 is mechanically connected to conductor 21, for example due to radial crushings as illustrated in FIG. 7, the plastic sheathing 22 can also be completely omitted. This applies for all embodiments.

Figure 8:
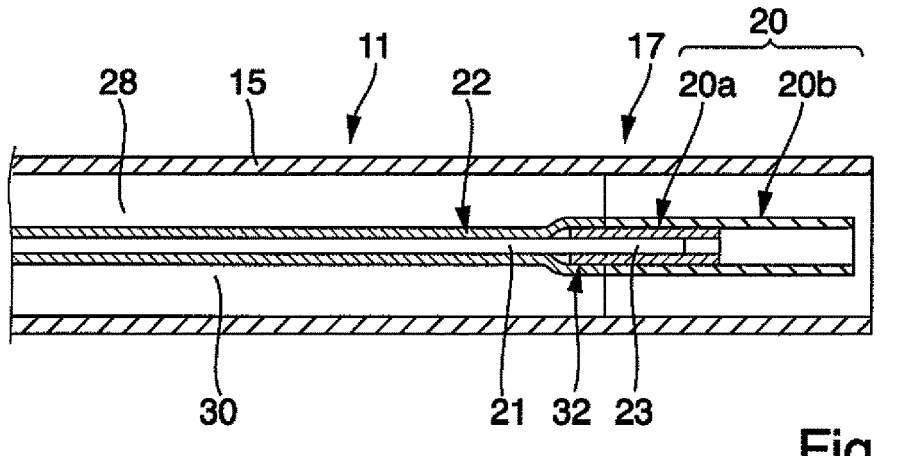

FIG. 8 illustrates another modification of the invention that can be used in all plasma probes 11 described herein. The electrode 20 consists of a first sleeve 20a that is located on the distal end 23 of conductor 21 and inserted into the plastic sheathing 22. On this sleeve 20a a second sleeve 20b is located that is, for example, welded or crimped to the sleeve 20a or is simply located in a friction-fit manner thereon. The two sleeves 20a, 20b consist preferably of different materials or material combinations. For example, the hollow cylindrical sleeve 20b can be silvered on its outer surface, whereby the plasma discharge is concentrated on the distal end thereof and the heat introduction in this sleeve 20b is minimized. On the contrary, sleeve 20a can consist of non-coated stainless steel with poor thermal conductivity, such that the heat introduction into the plastic sheathing 22 is minimized. Independent from the material selection, the thermal introduction into the plastic can be reduced by means of a distance between the sleeve 20b and the plastic sheathing 22.

The sleeve 20a and the joint between the sleeves 20a, 20b forms a thermal barrier between the part of the electrode 20 subject to the discharge and the remaining plasma probe 11. This increases the durability of electrode 20 and the entire plasma probe 11 on one hand due to the increase of the electrode surface and on the other hand, due to the reduction of the heat flow originating from electrode 20.

Figure 9:
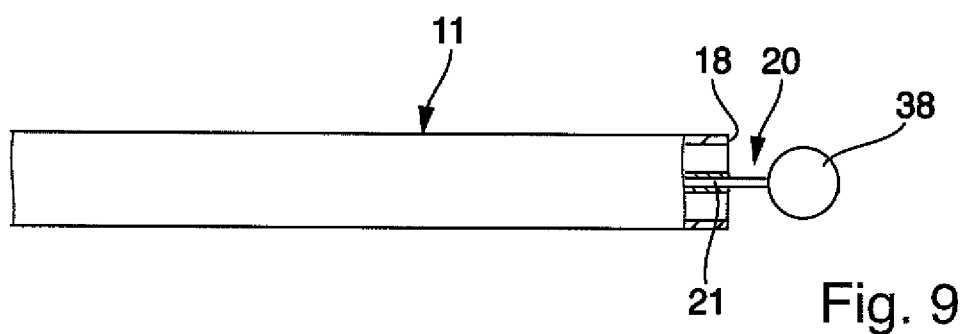

In all embodiments of plasma probe 11 described above it has been assumed that the electrode 20, 20' does not project beyond the distal face 18 of hose 15. However, based on any of the embodiments described above, plasma probes 11 can also be provided according to the example of FIG. 9. The electrode 20 that can be connected with the conductor 21 in any manner described above then projects beyond the face 18 in distal direction and can support an insulator body 38, made for example of ceramic or another temperature-resistant plastic. The insulator body 38 can thereby be formed in a ball-shaped, mushroom-shaped or any other manner and is supported by electrode 20.

Figure 10:
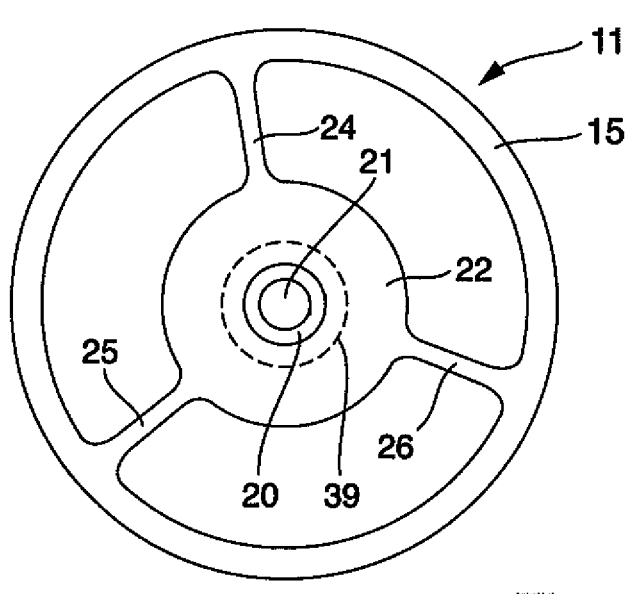
Figure 11:
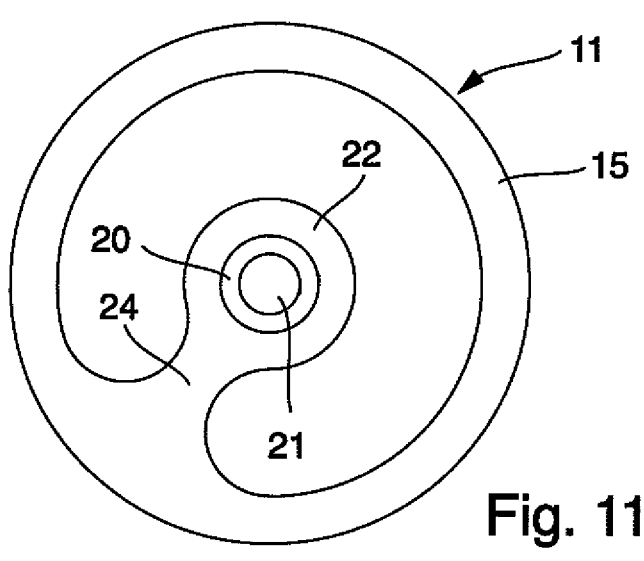

In terms of the configuration of the hose 15 and the plastic sheathing 22 numerous degrees of freedom exist. For example, the walls 24, 25, 26 can be arranged radially, as shown in FIG. 10. Also the conductor 21 can be surrounded by an insulation 39 first that is embedded in the plastic sheathing 22. In addition, the number of walls or other connections between the plastic sheathing 22 and the hose 15 can be defined different from the embodiments described above, as shown in FIG. 11. There, only one single connecting wall 24 is provided between the hose 15 and the plastic sheathing 22.

A plasma probe 11 according to one aspect of the invention comprises a hose with a conductor arranged therein that supports an electrode 20 at least at its distal end. The electrode 20 is either directly secured on the conductor 21 or the conductor 21 is provided with a plastic sheathing 22 at least at its distal end by means of which the electrode 20 is held. The electrode 20 can be inserted between the conductor 21 and the plastic sheathing 22 and can be clamped in this manner. After first use the plastic sheathing 22 can be fused to the electrode 20. In any case, the conductor 21 is placed with clearance inside a channel or hollow space of electrode 20, however, whereby also in case of spot-like contact between the conductor 21 and the electrode 20 due to the gap provided between them apart therefrom the heat transmission from the electrode 20 on the conductor 21 is impeded and thereby the heat introduction in the plasma probe 11 is limited. This benefits the lifetime of the plasma probe 11 and concurrently reduces its outer temperature and thus its sticking tendency to tissue. In doing so, the risk of an undesired perforation of sensitive or thin tissue layers is reduced. In addition, the concept according to the invention allows a long-term preservation of the roundness of the probe.

LIST OF REFERENCE SIGNS 11 plasma probe
12 apparatus
13 RF generator
14 gas source
15 hose
16 proximal end of hose 15
17 distal end of hose 15
18 distal face of hose 15
19 plasma exhaust port
20, 20' electrode
20a, 20b sleeves
21 conductor
22 plastic sheathing
23 distal end of conductor
24-26 walls
27 lumen
28-30 sub-lumina
31 distal end of electrode 20
32 proximal end of electrode 20
33 closed distal end of electrode 20
34 sleeve
35 tapering seat
36, 37 noses
38 insulator body

The invention claimed is:
1. A plasma probe (11) comprising: a hose (15) that comprises a proximal end (16) and a distal end (17) between which at least one lumen (27) is formed; an electrical conductor (21) arranged inside the hose (15) and extending from the proximal end (16) of the hose (15) up to its distal end (17) and that comprises a plastic sheathing (22); and an electrode (20) comprising a proximal end (32) electrically connected to the electrical conductor (21) and a distal end (33) extending in a distal direction; wherein the electrode (20) is held by at least one of the electrical conductor (21) and the plastic sheathing (22) of the electrical conductor (21); wherein the proximal end (32) of the electrode (20) extends into the plastic sheathing (22) of the electrical conductor (21) and is axially fixed thereby, wherein the electrode (20) comprises a first sleeve (20a) that is located on the distal end (23) of conductor (21) and is inserted into the plastic sheathing (22).

2. The plasma probe according to claim 1, wherein the at least one lumen (27) is connected to a gas source (14) at the proximal end (16) of the hose (15).

3. The plasma probe according to claim 1, wherein the electrical conductor (21) is connected to an electrical source (13) at a proximal end thereof.

4. The plasma probe according to claim 1, wherein the at least one lumen (27) is separated into two or more sub-lumina (28, 29) arranged parallel to one another.

5. The plasma probe according to claim 1, wherein the electrical conductor (21) is centrally arranged inside the hose (15).

6. The plasma probe according to claim 1, wherein the plastic sheathing (22) and the electrical conductor (21) arranged therein are movably arranged inside the hose (15).

7. The plasma probe according to claim 1, wherein the proximal end (32) of the electrode (20) connected with the electrical conductor (21) is hollow or an entirety of the electrode (20) is hollow, and the electrical conductor (21) extends within the electrode (20).

8. The plasma probe according to claim 1, wherein the electrode (20) comprises a coating.

9. The plasma probe according to claim 1, wherein the proximal end (32) of the electrode (20) extends between the electrical conductor (21) and the plastic sheathing (22).

10. The plasma probe according to claim 1, wherein the electrical conductor (21) is movably arranged in a longitudinal direction inside and relative to the electrode (20).

11. The plasma probe according to claim 1, wherein the electrode (20) is held on the electrical conductor (21) by plastic deformation.

12. The plasma probe according to claim 1, wherein the distal end (33) of the electrode (20) is provided with an insulator body (38).

13. The plasma probe according to claim 1, wherein the plastic sheathing (22) is connected to the hose (15) by at least one flexible wall (24) or by multiple flexible walls (24, 25, 26).

14. The plasma probe according to claim 13, wherein the electrical conductor (21) is supported inside the hose (15) exclusively by the at least one flexible wall (24) or the multiple flexible walls (24, 25, 26).

15. A method for assembly of an electrode (20) of a plasma probe (11) comprising the following steps:

arranging an electrical conductor (21) inside of a hose (15) that comprises a proximal end (16) and a distal end (17) between which a lumen (27) is formed, wherein the electrical conductor (21) extends from the proximal end (16) of the hose (15) up to its distal end (17) and comprises a plastic sheathing (22);

pushing a hollow end (32) of an electrode (20) on an end (23) of the electrical conductor (21); and inserting the hollow end (32) of the electrode (20) into the plastic sheathing (22) of the electrical conductor (21).

16. A plasma probe (11) comprising:

a hose (15) that comprises a proximal end (16) and a distal end (17) between which at least one lumen (27) is formed;

an electrical conductor (21) arranged inside the hose (15) and extending from the proximal end (16) of the hose (15) up to its distal end (17) and that comprises a plastic sheathing (22); and an electrode (20) comprising a proximal end (32) electrically connected to the electrical conductor (21) and a distal end (33) extending in a distal direction;

wherein the electrode (20) is held by at least one of the electrical conductor (21) and the plastic sheathing (22) of the electrical conductor (21);

wherein the proximal end (32) of the electrode (20) extends between the plastic sheathing (22) and the electrical conductor (21) and is axially fixed by the plastic sheathing (22).

* * * * *